United States Patent
Albrecht et al.

(10) Patent No.: US 7,192,597 B2
(45) Date of Patent: *Mar. 20, 2007

(54) COMPOSITION FOR TREATMENT OF SKIN, HAIR AND NAILS

(75) Inventors: Martin Albrecht, Moenchengladbach (DE); Miklos Ghyczy, Cologne (DE)

(73) Assignee: Kuhs GmbH, Loerrach (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/135,459

(22) Filed: May 24, 2005

(65) Prior Publication Data

US 2005/0208012 A1   Sep. 22, 2005

Related U.S. Application Data

(63) Continuation of application No. 10/203,993, filed as application No. PCT/DE01/00615 on Feb. 19, 2001, now Pat. No. 7,001,604.

(30) Foreign Application Priority Data

Feb. 25, 2000   (DE) .............................. 100 08 850.3

(51) Int. Cl.
  *A61K 8/00* (2006.01)
  *A61K 8/02* (2006.01)
  *A61K 8/04* (2006.01)
  *A61K 9/127* (2006.01)
  *A61K 38/00* (2006.01)

(52) U.S. Cl. ...................... 424/400; 424/401; 424/450; 514/2

(58) Field of Classification Search ................ 424/400, 424/401, 450; 514/2
See application file for complete search history.

(56) References Cited

U.S. PATENT DOCUMENTS 7,001,604 B2 *  2/2006  Albrecht et al. ............ 424/401

\* cited by examiner

*Primary Examiner*—Shelley A. Dodson
(74) *Attorney, Agent, or Firm*—Dennison, Schultz & MacDonald

(57) ABSTRACT

A composition, especially for treatment of aged and/or stressed skin, the composition containing, in addition to water, at least one substance that forms lamellar structures with water. The composition further contains S-adenosyl-methionine and/or at least one compound that contains a functional group of the general formula $-CH_2-N^{\oplus}-(CH_3)_3$. The lamellar structure has a layer structure in which an upper layer of the substance is aligned with a lower layer, the hydrophilic groups of the substance each point outwards, and the lipophilic groups of the substance are aligned inwards with one another. The lamellar structure is surrounded by a hydrophilic medium, preferably water.

48 Claims, No Drawings

COMPOSITION FOR TREATMENT OF SKIN, HAIR AND NAILS

This application is a continuation of U.S. application Ser. No. 10/203,993 filed Dec. 9, 2002, now U.S. Pat. No. 7,001,604. U.S. application Ser. No. 10/203,993 is a filing under 35 USC 371 of PCT/DE01/00615 filed Feb. 19, 2001.

Cosmetic compositions, in particular those cosmetic compositions which are used to care for and/or treat skin, and which are preferably used to care for and/or to treat aged skin and/or stressed skin, usually also have apart from water those substances which can form emulsions with water. Such an aqueous emulsion, which can be provided with a lipophilic additive if required, constitutes the simplest example of a cosmetic composition.

In addition, such a known cosmetic composition may contain still other cosmetic active ingredients, thickeners, gel forming agents, dyes, stabilizers, age-inhibitors and/or perfumes as well as pH value regulators.

It is also known that in the simplest case of a cosmetic composition the substance in this present composition can form with water lamellar structures under specific manufacturing provisions, such lamellar structures having a layer structure such that each upper layer of the substance is aligned with a lower layer of the substance. Here this alignment of the individual substance layers occurs depending on the respectively used solvent, such that the hydrophilic groups of the substance each point outwards, while the lipophilic groups are aligned inwards with one another, or that these lipophilic groups each point outwards, while the hydrophilic groups of the substance are aligned inwards. The latter is always the case when the medium surrounding the lamellar structure is lipophilic, while the former lamellar structure occurs whenever the substance is absorbed in a hydrophilic medium.

If two layers of the substance are oriented in the present sense, then this is referred to as a single membrane, while this lamellar structure is then referred to as a double membrane when two layer pairs are superposed.

The object of the present invention is to provide a cosmetic composition which has a particularly high cosmetic efficacy.

This problem is solved according to the present invention by a composition for treatement as of skin, hair and nails described herein.

The cosmetic composition according to the invention, which is applied in particular in the case of aged and/or stressed skin, has, apart from water, at least one substance forming lamellar structures with water. Furthermore, the inventive composition has at least one compound which has at least one functional group of the general formula I

$$—CH_2—N^{\oplus}—(CH_3)_3 \qquad \text{(formula 1)}$$

and/or contains at least one metabolite of this compound and/or S-adenosylmethionine.

In other terms, the cosmetic composition according to the invention in the simplest case thus comprises, apart from water, at least one substance forming lamellar structures with water and the afore mentioned compound which has the above mentioned functional group of the general formula I, and/or a metabolite of this compound and/or S-adenosylmethionine.

It was surprisingly found that the composition according to the present invention has a high cosmetic efficacy which is expressed on the one hand in a protective function of the skin and on the other hand in a healing function for aged, sick and/or stressed skin, so that skin treated with the inventive composition is or becomes flexible and smooth and aids already irritated and/or stressed skin to return to its original natural appearance and condition. Moreover, it was observed that aged skin returns to its taut and elastic condition, with particularly undesired wrinkles being smoothed out. After a few applications of the inventive cosmetic composition dried skin or roughened skin regained its natural and pliable appearance.

This positive and exemplary increased cosmetic efficacy of the cosmetic composition according to the invention is attributed to the fact that lamellar structures are present in the composition according to the present invention or develop during application of same, whereby the lamellar structures make their way into the intercellular lipids of the cornea where they have the effect of a sealing and healing substance, in particular where there is a disrupted barrier function of the skin. In addition to this, it is assumed that the lamellar structures transport S-adenosylmethionine and/or the compound, which has at least one functional group of the general formula I, and/or the metabolite thereof to the disturbed sites of the skin barrier, whereby the S-adenosylmethionine and/or the afore mentioned compound and/or its metabolite is or are eminently suited, to buffer the electrons occurring in the cell when the energy conversion is disturbed and generated to excess and/or the electrons generated at the wrong place and/or the missing and/or inadequate oxygen supply, which represent causing elements for all previously listed skin blemishes. These electrons and/or a disrupted oxygen supply and delivery to the cells of the skin are responsible, on account of the knowledge of the present invention, for damaging of the cells and thus also for an undesired skin change and/or skin damage, and constitute a substantial cause of rapid ageing of skin. It is also understood that the cosmetic composition according to the invention effectively and considerably delays ageing of the skin and associated undesired skin changes, so for example skin slackness or the formation of wrinkles. In particular, the combination of the substance forming the lamellar structures with the compound contained in the composition according to the present invention, which has at least one functional group of the general formula I, with a metabolite thereof and/or with S-adenosylmethionine ensures that S-adenosylmethionine and/or the compound also actually reaches where the afore mentioned buffering is to take place. This is attributed to the fact that S-adenosylmethionine and/or the compound is integrated in the substance forming the lamellar structures, whereby it is possible for both intercalation and/or accumulation of the S-adenosylmethionine and/or the compound and/or of the metabolite on the substance forming the lamellar structures and integration of the S-adenosylmethionine and/or the compound and/or of the metabolite into the lamellar structures formed by the substance in terms of mixed-lamellar structures.

Furthermore, the S-adenosylmethionine, and/or the compound having at least one functional group of the general formula I and/or its metabolites containing in the inventive composition functions by means of the at least one methyl group contained therein as electron acceptor and as oxygen substitute and thus traps excess electrons, not required for metabolism of the individual cell, whereby this methyl group or the corresponding methyl groups is or are converted into harmless methane.

This effect previously described in the inventive composition is all the more astonishing for the average expert since S-adenosylmethionine and also compounds with the functional group according to formula I and also its metabolites are very stable and break down outside the organism mass only under extreme thermal conditions. It is assumed here that due to the targeted and local application on the respectively damaged cell or cells those reaction conditions are created which enable the previously mentioned enzymatically caused conversion to methane.

In summary, the cosmetic composition according to the invention effectively prevents excess energy-rich electrons and their by-products, that is, oxygen radicals in particular, from forming at all, and/or other radicals attaching undesirably to skin, hair or nails and causing cellular change, damage and/or destruction here. In the biological cycle of skin, hair or nails the composition according to the present invention enters a preliminary stage, that is, such a stage where electrons and/or radicals acting from externally are present in excess or these electrons or radicals are misdirected, so that they are accordingly eliminated. Because the cosmetic composition according to the invention traps the excess energy-rich electrons and/or radicals and then converts these into non-toxic products and methane, damage to the cells or the skin barrier is prevented particularly effectively with application of the inventive composition.

Basically, the cosmetic composition according to the invention contains those substances forming lamellar structures as substance with water having a hydrophilic and at the same time a hydrophobic molecular group. Particularly preferred as this substance are monoglyceride, diglyceride, preferably distilled medium-chain monoglycerides, sphingolipids, phospholipids, fatty alcohols, fatty acids, soaps, mono- and/or di-esters of fatty acids, succrose, glucose and/or their derivates, glucosidic, furanosidic and/or pyranosidic condensation products of fatty alcohols with glucose and/or succrose and their polymer derivates, mono- and/or di-esters of glucosides with fatty acids derivates, sterols, mono- and/or di-esters of fatty acids and sterols and/or glycol derivates of sterols as a substance forming lamellar structures with water, whereby the fatty acids preferably have a $C_8$–$C_{22}$ saturated linear carbon chain.

However, it is especially suitable if at least one hydrogenated phospholipid, and in particular a hydrogenated phosphatidylcholine, is contained in the cosmetic composition according to the invention as substance which is in a position to form lamellar structures with water. Here, such hydrogenated phospholipids and in particular hydrogenated phosphatidylcholine on the one hand forms lamellar structures with water and on the other hand these lamellar structures are eminently suited to immigrate into the intercellular lipids of the cornea and at the same time provide large quantities of the compound contained in the cosmetic composition according to the invention, of the metabolite and/or of S-adenosylmethionine, whereby the especially high efficacy of this preferred embodiment of the cosmetic composition according to the invention become clear.

The afore mentioned advantages are integral to those further developments of the composition according to the present invention, which contain as substance a hydrogenated phospholipid which exhibit at least 60% by weight and preferably between 70% by weight and 95% by weight hydrogenated phosphatidylcholine, whereby these concentration data refer to the concentration of the hydrogenated phospholipids in the ready-to-use (finished) composition.

With respect to the concentration of the at least one substance, which can form lamellar structures with water contained in the cosmetic composition according to the invention, it is generally held that this concentration is directed at the storage and transport capacity of the lamellar structure correspondingly to be formed for the compound, its metabolite and/or for the S-adenosylmethionine. In particular, this at least one substance is present in the cosmetic composition according to the invention in a concentration between 0.01% by weight and 10% by weight, preferably in a concentration between 2% by weight and 7% by weight, whereby these concentration data refer to the ready-to-use cosmetic composition.

With respect to the compound and/or the metabolite contained in the composition according to the present invention it is to be stressed that preferably the metabolite or the compound, containing at least one functional group of the present general formula 1, is the type of metabolite or compound which occurs naturally in aerobic cells, in particular in the cell membranes. It should also be emphasized here that as a compound the inventive composition should not exhibit those chemical constituents which are designated in the technology to a large extent as quaternary ammonium compounds and which constitute synthetic interface-active substances.

It is particularly advantageous if the composition according to the present invention contains as a compound betaine, acetyl choline, N-acetyl-ethanolamine, choline, glycerophosphocholine, phosphatidylcholine, lysophosphatidylcholine, carnitine, acyl carnitine, sphingomyelines alone or in a mixture thereof and/or derivatives and/or metabolites thereof.

In connection with the cosmetic composition according to the invention it has been and will continually be mentioned that this can have selectively or in addition at least one metabolite of the compound contained in the composition according to the present invention with the functional group reproduced in formula 1. Preferred metabolites of this compound are in particular methyl glycine, dimethyl glycine and methyl methionine, so that accordingly particularly suitable embodiments of the inventive cosmetic composition can then contain as a metabolite methyl glycine, dimethyl glycine and/or methyl methionine.

Depending on the respective application the concentration of the compound aligns with the functional group reproduced in formula 1 and/or its metabolites and/or the concentration of S-adenosylmethionine contained in the inventive composition, varies. It is particularly preferred if the compound and/or its metabolites and/or S-adenosylmethionine is present in a concentration between 0.0001% and 10%, preferably between 0.1% and 9%, relative to the weight of the ready-to-use composition.

An embodiment of the cosmetic composition according to the invention having a particularly high cosmetic efficacy provides that the composition contains a mixture comprising betaine, methyl glycine, N-acetyl ethanolamine and/or inositol as constituents. This configuration can have selectively either all four afore mentioned preferred constituents or only three or two constituents of the afore mentioned type, thus in particular the combination of betaine and methyl glycine, the combination of N-acetyl ethanolamine and methyl glycine, the combination of inositol and methyl glycine, the combination of betaine and N-acetyl ethanolamine as well as the combination of betaine with N-acetyl ethanolamine and the combination of betaine with N-acetyl ethanolamine and methyl glycine.

If the previously described embodiment of the cosmetic composition according to the invention contains a mixture of two of the afore mentioned special constituents, the mol-mass ratio of these two constituents (betaine, methyl glycine, N-acetyl-ethanolamine, inositol) varies in particular between 1:1 to 1:9.

A particularly suitable and advantageous further embodiment of the cosmetic composition according to the invention provides that the inventive cosmetic composition has, apart from water, the substance forming lamellar structures, the compound and/or the metabolite and/or S-adenosylmethionine, also at least one cosmetic active ingredient, whereby in particular such a cosmetic active ingredient is contained in the inventive composition, which maintains skin, hair and/or nails in good and healthy conditions.

Included as a cosmetic active ingredient in particular are those active ingredients which effect cleaning and care of the skin and maintenance of a healthy skin condition, external protection of the skin from damaging environmental influences, climatic and actinitic influences, thus in particular with excessive solar and UV radiation, protection of skin from laundry and cleansing agents as well as other environmental stress, thus in particular dust and emissions. Belonging to these in particular are unsaturated fats having a pliable effect, liquid fatty acid esters and hydrocarbons with short-chain branching which have a spreading effect, covering and protective fats, in particular comprising oils, liquid fatty alcohols, silicon oils, solid fatty acid esters and/or fatty alcohols, whereby preferably an oil and/or an oil constituent, in particular also the unsaponifiable portions of a plant oil, such as preferably avocado oil, olive oil and/or at least one native oil is contained as a cosmetic active ingredient in the cosmetic composition according to the invention. In addition, vitamins, oligoproteins, collagen-hydrolysates and known and useful UV filter substances are also to be mentioned as cosmetic active ingredients.

If the inventive composition is used in the area of cosmetic treatment of hair and nails, these embodiments of the cosmetic composition according to the invention preferably contain, apart from thickeners and binders, in particular based on natural polymers, also back-greasing substances such as Vaseline, paraffin oils, cetyl alcohols, polysiloxanes and/or lanoline.

In particular, the concentration of the afore mentioned maintaining and caring active ingredients contained in the composition according to the present invention are between 1% and 55% and in particular between 5% and 30%, relative to the weight of the ready-to-use cosmetic composition.

In another embodiment of the cosmetic composition according to the invention this has in addition to the afore mentioned maintaining active ingredients or instead of the afore mentioned maintaining active ingredients in particular at least one further active ingredient, whereby this is preferably such an active ingredient which increases the moisture of the skin when applied topically. Preferred examples of such an active ingredient increasing the skin moisture are generally N-acyl-alkanolamines, preferably lactamide MEA, oleamide MEA and/or acetamide MEA, and in particular N-acyl-ethanolamines, so in particular N-acetyl-phosphatidylethanolamine, N-acetyl-ethanolamine already mentioned several times hereinabove, N-oleoyl-ethanolamine, N-linolenoyl-ethanolamine as well as N-acyl-ethanolamine and/or N-acyl-2-hydroxy-propylamine, whereby the latter two ingredients contain fatty acids of cocoa fat and/or palm oil as acyl residues.

The concentration of these active ingredients in the composition according to the present invention increasing skin moisture varies preferably between 0.5% and 20%, relative to the weight of the ready-to-use (finished) cosmetic composition.

In a particularly advantageous further development of the above mentioned embodiments of the composition according to the present invention this development has as compound a fatty acid, a fatty acid salt and/or a mixture of betaine with at least one fatty acid and/or a mixture of betaine with at least one fatty acid salt.

Preferably such a salt is selected here as a fatty acid salt, in which the fundamental fatty acid is a linear fatty acid and has between 12 to 22 carbon atoms, while a fatty acid preferably likewise contains between 12 and 22 carbon atoms.

Particularly suitable fatty acid salts of betaine are betaine laurate, betaine myristate, betaine palmitate, betaine stearate, betaine oleate and betaine linolate, alone or in a mixture. It could be established surprisingly here that despite their relatively poor water solubility these afore mentioned fatty acid salts of betaine impart a particularly high cosmetic efficacy to the composition according to the present invention.

As already detailed before, the cosmetic composition according to the invention contains water, whereby the concentration of the water in the composition according to the present invention varies in particular between 5% and 90%, relative to the weight of the ready-to-use cosmetic composition.

The term water used in the present application covers all aqueous systems, in particular sterilized water, deionised water, distilled water and aqueous solutions and/or aqueous buffer systems.

Further, depending on the type of each selected formulation, the cosmetic composition according to the invention can contain at least one preservative, antioxidant, thickener, gel-forming agent and/or alcohol, preferably a multivalent alcohol.

A particularly preferred and multi-applicable formulation of the composition according to the present invention contains between 5% and 90% water,
0.01% and 10% substance forming lamellar structures,
0.0001% to 10% of the compound and/or its metabolites and/or of S-adenosylmethionine,
0.5% to 20% of active ingredient increasing skin moisture,
1% to 55% of at least one maintaining active ingredient as well as the usual other constituents in a concentration between 0% and 10 l, whereby the previously used term other constituents cover, in particular preservative, an antioxidant, a thickener, a gel-forming agent and/or an alcohol, preferably a multivalent alcohol. The above mentioned concentration data refer respectively to the weight of the ready-to-use composition.

The cosmetic composition according to the invention can basically be made up in each formulation suitable for topical application, whereby the cosmetic composition according to the invention is especially formulated as a topically applicable cream. This topically applicable cream has a viscosity at 20° C. between 4000 Pas and 40000 mPas, preferably between 12000 mPas and 25000 mPas, so that a cream thus formulated can be distributed easily and particularly smoothly over the skin.

To ensure the cosmetic efficacy of the inventive composition in particular for sensitive skin also or for sensitive hair or sensitive nails, the composition according to the present invention preferably has a pH value which varies between 4.0 and 7.2.

As already detailed initially with the composition according to the present invention, as cause for the improved cosmetic efficacy of the composition according to the present invention it is assumed that the inventive composition contains at least one of such a substance which forms lamellar structures. In particular, whenever the composition has between 15% by weight and 95% by weight, preferably between 30% by weight and 95% by weight, of such lamellar structures, whereby the afore mentioned concentrations refer to the weight of the substance contained in the composition according to the present invention, which is in a position to form lamellar structures, such a configuration has a particularly high cosmetic efficacy, because due to the high concentration of lamellar structures the integrated compound, containing at least one functional group of the general formula 1, and/or a metabolite hereof and/or integrated S-adenosylmethionine are transported in particularly high concentrations and particularly rapidly into the intercellular lipids of the cornea, such that the reactions described initially in the composition according to the present invention can take place particularly quickly.

Preferably the composition according to the present invention exhibits such lamellar structures having a thickness varying between 20 nm and 3 μm, in particular between 40 nm and 1 μm.

Inositol, as referred to hereinabove and hereinbelow, is to be designated correctly in chemical terms as inosite (cyclohexane-1,2,3,4,5,6-hexaole).

In particular, a salt of methyl methionine and preferably S-methyl-DL-methionine-sulfonium chloride is used as methyl methionine in the composition according to the present invention and in the examples described hereinbelow.

The composition according to the present invention is explained in greater detail with reference to nine examples.

EXAMPLE 1

Examples 1 describes a cream for extremely stressed aged skin.

A cosmetic composition is prepared from the following list of contents:

| Phase 1 | |
| --- | --- |
| hydrogenated phosphatidylcholine, concentration of hydrogenated phosphatidylcholine 90% by weight | 2.0 g |
| monoglyceride C 12 | 1.5 g |
| olive oil | 17.0 g |
| cholesterol | 2.0 g |
| ceramide 3 | 0.1 g |
| avocadine | 1.0 g |
| squalene | 1.0 g |
| pentylene glycol | 5.0 g |
| palmitic acid | 1.0 g |
| Phase 2 | |
| acetamide MEA | 0.5 g |
| betaine, water-free | 0.8 g |
| carnitine | 0.5 g |
| water DAB 10 | ad 100.0 g |

Phase 1 and Phase 2 were first heated to 75° C. for production. Then Phase 2 was slowly added to Phase 1 while the temperature was maintained and the mixture was continuously stirred. After a complete mixture was prepared it was then homogenized for two minutes at 15000 rpm using a homogenizer (Ultra Turrax).

This homogenizing was followed by forced homogenizing by means of high-pressure homogenisation lasting five minutes at 790 bar. The mixture was then cooled to 0.37° C. with continuous stirring. The mixture was then homogenized again for three minutes using an Ultra Turrax homogenizer at 8000 rpm. After this the mixture was cooled down to room temperature with continuous stirring.

EXAMPLE 2

Example 2 describes a body lotion for skin which tends to barrier disruptions, whereby the body lotion was prepared from the following constituents:

| Phase 1 | |
| --- | --- |
| hydrogenated phosphatidylcholine, concentration of hydrogenated phosphatidylcholine 90% by weight | 1.5 g |
| monoglyceride C 10 | 1.2 g |
| olive oil | 18.0 g |
| cholesterol | 1.0 g |
| ceramide 3 | 0.1 g |
| squalene | 1.0 g |
| benzyl alcohol | 1.0 g |
| palmitic acid | 1.0 g |
| Phase 2 | |
| lactamide MEA | 0.5 g |
| betaine, water-free | 1.0 g |
| choline, water-free | 0.2 g |
| water DAB 10 | ad 100.0 g |

Phase 1 and Phase 2 were first heated to 75° C. for production. Then Phase 2 was slowly added to Phase 1 while the temperature was maintained and the mixture was continuously stirred. After a complete mixture was prepared it was then homogenized for two minutes at 10000 rpm using a homogenizer (Ultra Turrax).

This homogenizing was followed by forced homogenizing by means of high-pressure homogenisation lasting five minutes at 600 bar. The mixture was then cooled to 37° C. with continuous stirring. The mixture was then homogenized again for three minutes using an Ultra Turrax homogenizer at 8000 rpm. After this the mixture was cooled down to room temperature with continuous stirring.

EXAMPLE 3

A body spray for extremely stressed skin was prepared using the following constituents:

| Phase 1 | |
| --- | --- |
| hydrogenated phosphatidylcholine, concentration of hydrogenated phosphatidylcholine 90% by weight | 2.0 g |
| monoglyceride C 16 | 1.8 g |
| olive oil | 17.0 g |
| cholesterol | 2.0 g |
| ceramide 3 | 0.1 g |
| avocadine | 1.0 g |
| squalene | 1.0 g |
| pentylene glycol | 5.0 g |
| betaine palmitate | 1.8 g |
| Phase 2 | |
| acetamide MEA | 0.5 g |
| water DAB 10 | ad 100.0 g |

Phase 1 and Phase 2 were first heated to 75° C. for production. Then Phase 2 was slowly added to Phase 1 while the temperature was maintained and the mixture was continuously stirred. After a complete mixture was prepared it was then homogenized for two minutes at 15000 rpm using a homogenizer (Ultra Turrax).

This homogenizing was followed by forced homogenizing by means of high-pressure homogenisation lasting five minutes at 790 bar. The mixture was then cooled to 37° C. with continuous stirring. The mixture was then homogenized again for three minutes using an Ultra Turrax homogenizer at 8000 rpm. After this the mixture was cooled down to room temperature with continuous stirring.

EXAMPLE 4

Example 4 describes a cream for skin tending to barrier disruptions.

A cosmetic composition was prepared from the following list of constituents:

| Phase 1 | |
|---|---|
| hydrogenated phosphatidylcholine, concentration of hydrogenated phosphatidylcholine 90% by weight | 2.0 g |
| distilled monoglyceride C 10 | 1.7 g |
| olive oil | 20.0 g |
| pentylene glycol | 5.0 g |
| palmitic acid | 2.2 g |
| Phase 2 | |
| palmitamide MEA | 0.5 g |
| betaine, water-free | 0.8 g |
| choline | 0.2 g |
| water DAB 10 | ad 100.0 g |

Phase 1 and Phase 2 were first heated to 75° C. for production. Then Phase 2 was slowly added to Phase 1 while the temperature was maintained and the mixture was continuously stirred. After a complete mixture was prepared it was then homogenized for two minutes at 15000 rpm using a homogenizer (Ultra Turrax).

This homogenizing was followed by forced homogenizing by means of high-pressure homogenisation lasting five minutes at 790 bar. The mixture was then cooled to 37° C. with continuous stirring. The mixture was then homogenized again for three minutes using an Ultra Turrax homogenizer at 8000 rpm. After this the mixture was cooled down to room temperature with continuous stirring.

EXAMPLES 5 TO 9

The following examples 5 to 9 describe a cream for use both with stressed skin and irritated skin, in particular for aged skin.

A cosmetic composition was prepared from the following list of constituent, whereby all examples 5 to 9 have identical Phases 1 and 2, but a different Phase 3.

Phase 1 had the following contents identical throughout examples 5 to 9:

| Phase 1 | |
|---|---|
| hydrogenated phosphatidylcholine, concentration of hydrogenated phosphatidylcholine 90% by weight | 1.95% |
| olive oil (C 16:0, C 18:1) | 19.2% |
| C 18:1 triglyceride | 3.9% |
| C 16:0 triglyceride | 3.9% |
| Phase 2 | |
| sodium carbomer | 0.24% |
| xanthan gum | 0.1% |
| pentylene glycol | 5.0% |

| -continued | |
|---|---|
| glycerine | 5.9% |
| hydroxy ethyl cellulose | 0.2% |
| water | ad 100.0% |

The above mentioned and the following percentages all refer to % by weight.

Example 5 contained a Phase 3 having the following contents:

| Phase 3 | |
|---|---|
| acetamide MEA | 0.5% |
| betaine | 0.3% |

Example 6 contained a Phase 3 having the following contents:

| Phase 3 | |
|---|---|
| acetamide MEA | 0.5% |
| methyl glycine (sarcosine) | 0.2% |

Example 7 contained a Phase 3 having the following contents:

| Phase 3 | |
|---|---|
| acetamide MEA | 0.5% |
| betaine | 0.3% |
| methyl glycine (sarcosine) | 0.2% |

Example 8 contained a Phase 3 having the following contents:

| Phase 3 | |
|---|---|
| betaine | 0.3% |
| methyl glycine (sarcosine) | 0.2% |

Example 9 contained a Phase 3 having the following contents:

| Phase 3 | |
|---|---|
| betaine | 0.5% |
| methyl methionine | 0.2% |
| methyl glycine (sarcosine) | 0.2% |

The above mentioned percentages of contents given for Phase 3 of examples 5 to 9 refer to the ready-to-use cosmetic composition.

Phase 1 and Phase 2 were first heated separately to 75° C. to produce the compositions described in examples 5 to 9. Then Phase 2 was slowly added to Phase 1 while the temperature was maintained and the mixture was continuously stirred. After a complete mixture was prepared it was then homogenized for two minutes at 16000 rpm using a homogenizer (Ultra Turrax).

The mixture prepared from Phases 1 and 2 was then cooled to 37° C. with continuous stirring. Then Phase 3 was slowly added to the mixture of Phases 1 and 2 while the temperature was maintained and the mixture was continuously stirred.

The mixture was then homogenized again for five minutes using an Ultra Turrax homogenizer at 5000 rpm. After this the mixture was cooled down to room temperature with continuous stirring to form the respective composition.

The terminology used in the examples corresponds insofar as it does not relate to unambiguous chemical terms as used in "International Cosmetic Ingredient Dictionary and Handbook", 7$^{th}$ edition, published by "The Cosmetic, Toiletry, and Fragrance Association, Washington D.C." (CTFA).

The invention claimed is:

1. A composition for healing stressed or sick skin, comprising:
 a) at least one substance which forms lamellar structures with water, said substance being selected from the group consisting of monoglycerides, diglycerides, distilled medium-chain monoglycerides, sphingolipids, phospholipids, fatty alcohols, fatty acids, soaps, mono-esters of fatty acids, di-esters of fatty acids, sucrose, glucose, glucosidic condensation products of fatty alcohols with glucose and/or sucrose, furanosidic condensation products of fatty alcohols with glucose and/or sucrose, pyranosidic condensation products of fatty alcohols with glucose and/or sucrose, mono-esters of glucosides with fatty acid derivates, di-esters of glucosides with fatty acid derivates, sterols, mono-esters of fatty acids and sterols, di-esters of fatty acids and sterols, glycol derivates of sterols, and mixtures thereof;
 b) S-adenosylmethionine and/or at least one compound which has at least one functional group of general formula I:

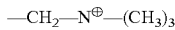  (formula I)

said at least one compound excluding quaternary ammonium surfactants and being selected from the group consisting of betaine, acetyl-choline, choline, glycerophosphocholine, phosphatidylcholine, lysophosphatidylcholine, carnitine, acylcarnitine, sphingomyelne, and mixtures, derivates and metabolites thereof;
 c) a hydrophilic medium, and
 d) an additive selected from the group consisting of methyl glycine, dimethyglycine, methyl methionine and mixtures therefore,
 wherein said composition comprises a lamellar structure having a layer structure in which an upper layer of said substance is aligned with a lower layer of said substance, hydrophilic groups of said substance each point outwards and lipophilic groups of said substance are aligned inwards with one another, and said lamellar structure is surrounded by said hydrophilic medium.

2. The composition according to claim 1, wherein the hydrophilic medium is water.

3. The composition according to claim 1, wherein said lamellar structure forms one single membrane comprising only said upper layer and said lower layer.

4. The composition according to claim 1, wherein said lamellar structure forms a double membrane comprising two superposed layer pairs.

5. The composition according to claim 1, wherein the substance is a hydrogenated phospholipid.

6. The composition according to claim 5, wherein the hydrogenated phospholipid is a hydrogenated phosphatidylcholine.

7. The composition according to claim 5, wherein the hydrogenated phospholipid contains at least 60% by weight of hydrogenated phosphatidylcholine.

8. The composition according to claim 1, wherein the substance is present in a concentration between 0.01 and 10% by weight.

9. The composition according to claim 8, wherein the substance is present in a concentration between 2 and 7% by weight.

10. The composition according to claim 1, wherein the compound is a natural compound or a metabolite thereof present in aerobic cells.

11. The composition according to claim 1, wherein the S-adenosylmethionine and/or said compound is present in the composition in a concentration between 0.0001 and 10% by weight.

12. The composition according to claim 11, wherein the S-adenosylmethionine and/or said compound is present in the composition in a concentration between 0.1 and 9% by weight.

13. The composition according to claim 1, additionally comprising a mixture of compounds selected from the group consisting of betaine, methyl glycine, N-acetyl-ethanolamine and inositol.

14. The composition according to claim 13, wherein two said compounds are present in a ratio of mol masses between 1:1 and 1:9.

15. The composition according to claim 1, wherein the additive is present in a concentration between 0.0001 and 10% by weight.

16. The composition according to claim 15, wherein the additive is present in a concentration between 0.1 and 9% by weight.

17. The composition according to claim 1, additionally comprising at least one active ingredient.

18. The composition according to claim 17, wherein the active ingredient is an active ingredient for maintaining the skin in good and healthy condition.

19. The composition according to claim 17, wherein the active ingredient is an oil, an oil constituent or a mixture thereof.

20. The composition according to claim 19, wherein the oil is at least one native oil.

21. The composition according to claim 20, wherein the native oil is olive oil.

22. The composition according to claim 19, wherein the oil constituent is an unsaponifiable portion of avocado oil.

23. The composition according to claim 18, wherein the active ingredient is present in a concentration between 1 and 55% by weight.

24. The composition according to claim 17, wherein the active ingredient is for maintaining skin moisture.

25. The composition according to claim 24, wherein the active ingredient is an amide.

26. The composition according to claim 25, wherein the amide is an alkanolamide.

27. The composition according to claim 26, wherein the alkanolamide is selected from the group consisting of lactamide MEA, palmitamide MEA, oleamide MEA, acetamide MEA and mixtures thereof.

28. The composition according to claim 24, wherein the active ingredient is present in a concentration between 0.5 and 20% by weight.

29. The composition according to claim 1, additionally comprising a fatty acid, a fatty acid salt or a mixture thereof.

30. The composition according to claim 1, wherein said compound having at least one functional group of formula I is at least one fatty acid salt of betaine.

31. The composition according to claim 1, wherein said compound having at least one functional group of formula I is a mixture of betaine with at least one fatty acid.

32. The composition according to claim 1, wherein said compound having at least one functional group of formula is a mixture of betaine with at least one fatty acid salt.

33. The composition according to claim 29, wherein the fatty acid or the fatty acid salt has a main carbon chain with 12 to 22 carbon atoms.

34. The composition according to claim 30, wherein said fatty acid salt of betaine is selected from the group consisting of betaine laurate, betaine myristate, betaine palmitate, betaine stearate, betaine oleate, betaine linolate and mixtures thereof.

35. The composition according claim 1, wherein said water is present in a concentration between 5 and 90% by weight.

36. The composition according to claim 1, additionally comprising at least one further component selected from the group consisting of a preservative, an antioxidant, a thickener, a gel-forming agent and an alcohol.

37. The composition according to claim 36, wherein the alcohol is a multivalent alcohol.

38. The composition according to claim 1, which contains, by weight:
to 90% water,
0.01 to 10% of said substance forming lamellar structures,
0.0001 to 10% of said S-adenosylmethionine, said at least one compound, or a mixture thereof,
0.0001 to 10% of an additive selected from the group consisting of methyl glycine, dimethylglycine, methyl methionine and mixtures thereof,
0.5 to 20% of an active ingredient increasing skin moisture,
1 to 55% of at least one active ingredient maintaining the skin in good and healthy condition, and
0 to 10% of other cosmetic components.

39. The composition according to claim 1, in the form of a topically applied cream with a viscosity at 20° C. of between 4000 mPas and 40000 mPas.

40. The composition according to claim 39, wherein the viscosity at 20° C. is between 12000 mPas and 25000 mPas.

41. The composition according to claim 1, having a pH value between 4.0 and 7.2.

42. The composition according to claim 1, which has lamellar structures in a concentration of between 15 and 95% relative to the weight of said substance forming the lamellar structures.

43. The composition according to claim 42, wherein the lamellar structures are present in a concentration of between 30% and 95% relative to the weight of said substance forming the lamellar structures.

44. The composition according to claim 1, wherein the lamellar structures have a thickness between 40 nm and 1 μm.

45. The composition according to claim 1, wherein the lamellar structures have a thickness between 20 nm and 3 μm.

46. A method for healing stressed skin, comprising applying to the stressed skin a plurality of times a composition according to claim 1.

47. A method for healing rough skin, comprising applying to the rough skin a plurality of times a composition according to claim 1.

48. A method for healing irritated skin, comprising applying to the irritated skin a plurality of times a composition according to claim 1.

* * * * *